United States Patent [19]

Kennedy

[11] Patent Number: 4,623,666

[45] Date of Patent: Nov. 18, 1986

[54] PHARMACOLOGICAL APPLICATIONS OF DIPHENYLHALONIUM ION

[76] Inventor: Thomas P. Kennedy, 3201 N. Charles St., Baltimore, Md. 21218

[21] Appl. No.: 668,810

[22] Filed: Nov. 6, 1984

[51] Int. Cl.$^4$ ............................................. A61K 31/03
[52] U.S. Cl. .................................................. 514/754
[58] Field of Search ........................ 514/754, 568, 709

[56] References Cited

U.S. PATENT DOCUMENTS

| | | | |
|---|---|---|---|
| 3,862,333 | 1/1975 | Chalupa et al. | 424/353 |
| 3,885,036 | 5/1975 | Moyle et al. | 424/275 |
| 3,981,897 | 9/1976 | Crivello | 260/440 |
| 4,151,175 | 4/1979 | Crivello et al. | 260/326 |
| 4,173,551 | 11/1979 | Crivello | 260/18 EP |
| 4,216,288 | 8/1980 | Crivello | 430/280 |
| 4,234,732 | 11/1980 | Crivello | 546/174 |
| 4,238,394 | 12/1980 | Crivello et al. | 260/326 |
| 4,264,703 | 4/1981 | Crivello | 430/270 |

OTHER PUBLICATIONS

J. Med. Chem. vol. 9, pp. 228–231 (1966)—Wiley et al.
Xenobiotica, 1979, No. 9, 539–546, Some Aspects of the Pharmacology of Diphenyleneiodonium, A Bivalent Iodine Compound.
The Journal of Biological Chemistry, vol. 218, No. 17, Sep. 10, 1974, pp. 6050–6056 Mechanism of Action of the Hypoglycemic Agent Diphenyleneiodonium.
Journal of Animal Science, vol. 46, No. 3, 1977 "Manipulating Rumen Fermentation.
Journal of Animal Science, vol. 49, No. 4, 1979 "Chemical Inhibition of Amino Acid Deamination by Ruminal Microbes in vitro[1,2].
Journal of Cardiovascular Pharmacology 2:247–255, 1980 Raven Press, New York Hypotensive Effects of N,N-Di-n-Propyldopamine in the Anestetized Dog: Comparison with Sodium Nitroprusside.
PBDA in Dog and Man/Fennel et al. Circulation vol. 67, No. 4, Apr. 1983 Propylbutyldopamine: Hemodynamic Effects in Conscious Dogs, Normal Human Volunteers and Patients with Heart Failure.
Medical Intelligence–Cohn and Fraciosa, vol. 297, No. 1, Jul. 7, 1977 "Drug Therapy, Vasodilator Therapy of Cardiac Failure" (Part 1).
Medical Intelligence, The New England Journal of Medicine, Aug. 4, 1977 "Drug Therapy, Vasodilator Therapy of Cardiac Failure (Part 2).
Progress in Cardiovascular Diseases, vol. XXIV, No. 5, Mar./Apr. 1982.
Jul. 1981, The American Journal of Medicine, vol. 71, "Physiologic Basis of Vasodilator Therapy for Heart Failure".
N-Acetylcysteine Potentiates Inhibition of Platelet Aggregation by Nitroglycerin—J. Loscaizo vol. 76, pp. 703–708—Aug. 1985.
A Structurally Novel Stimulator of Guanylate Cyclase with Long-Lasting Hypotensive Activity in the Dog—D. Pettibone et al. European Journal of Pharmacology 116 (1985) 307–312.
P. 1694 from Webster's Third New International Dictionary (1976).
Excerpt from Gould Medical Dictionary.

*Primary Examiner*—Douglas W. Robinson
*Attorney, Agent, or Firm*—Schwartz, Jeffery, Schwaab, Mack, Blumenthal & Evans

[57] ABSTRACT

Methods are disclosed for employing diphenylhalonium ion to elicit sodium nitroprusside-like effects in vivo, and to enhance cardiac contractility.

27 Claims, 8 Drawing Figures

4.4 mg/kg i.v.

PHARMACOLOGICAL APPLICATIONS OF DIPHENYLHALONIUM ION

BACKGROUND OF THE INVENTION

This invention relates to methods for employing diphenylhalonium ion to elicit various pharmacological effects treating different types of cardiovascular dysfunction. In accordance with the present invention, diphenylhalonium ion has been found to be useful in stimulating guanylate cyclase activity, increasing the contractility of cardiac muscle and inhibiting the aggregation of blood platelet cells, each effect being desirable in ameliorating symptoms associated with particular pathogical or pathogenic conditions.

Sodium nitroprusside (SNP), administered intravenously, is an extremely potent relaxant of vascular smooth muscle in both arterial and venous vessels. Prolonged administration of SNP can lead to symptoms of thiocyanate toxicity. Thyroid hormone insufficiency has also been reported during prolonged infusions of SNP. Nevertheless, SNP has become the drug of choice for treating hypertensive crises, and is also widely used in the acute management of cardiac failure. The potent activity in vivo of SNP has been linked to the drug's ability to stimulate guanylate cyclase in most mammalian tissues. The resulting elevation of guanosine 3',5'-cyclic phosphoric acid (cyclic guanosine monophosphate, hereinafter "cyclic GMP") levels can result, for example, in a relaxation of vascular smooth muscle and a decrease in the tendency for blood platelet cells to aggregate. See, e.g., Bohme et al, "Effects of sodium nitroprusside and other smooth muscle relaxants on cyclic GMP formation in smooth muscle and platelets," ADV. CYCLIC NUCLEOTIDE RES. 9: 131-43 (1978).

Although SNP is used to treat cardiac failure from a variety of causes, the cardiac glycosides, such as digitalis, still play a principal role in the treatment of chronic heart failure, in part because they can be taken orally, unlike SNP, which must be administered intravenously. But in addition to a comparatively narrow toxic-to-therapeutic ratio, cardiac glycosides also generally display a relatively weak inotropic effect. This deficiency in the pharmacological profile of cardiac glycosides has prompted an ongoing search for potent inotropic agents that can be employed in the management of severe congestive heart failure. See Baim et al, "Evaluation of a new bipyridine inotropic agent—Milrinone—in patients with severe congestive heart failure," NEW ENGL. J. MED. 309: 748-56 (1983).

Ideally, a single hemodynamic agent would combine SNP-like activity with inotropic activity, and would be suitable for administration by more than one route, e.g., orally as well as intravenously. Such an agent would be extremely useful in treating heart failure, since it could act to increase the force of contraction of the failing ventricle while concomitantly decreasing the total peripheral resistance against which the weakened heart must work. See Cohn and Franciosa, "Vasodilator therapy of cardiac failure," NEW ENGL. J. MED. 297: 27-31, 254-58 (1977). To the extent that the agent's SNP-like activity included elevating cGMP levels in blood platelets, the agent could also inhibit platelet aggregation, thereby ameliorating the atherosclerotic condition which is often present in patients with heart failure and to which platelet aggregation contributes.

While there is an extensive literature concerning candidates for therapeutic hemodynamic agents, there has apparently been no recognition in the art of pharmacological activity for diphenylhalonium-based compounds in this regard. One bivalent iodine compound, diphenyleneiodonium, and several of its derivatives have been identified as potent hypoglycemic agents, causing substantial, irreversible decreases of sugar levels in the blood of several animal species when administered orally in relatively low dosages. Gatley and Martin, "Some aspects of the pharmacology of diphenyleneiodonium, a bivalent iodine compound," XENOBIOTICA 9: 539-46 (1979). At the cellular level, diphenyleneiodonium catalyzes an exchange of $Cl^-$ and $OH^-$ ions across biological membranes, and, independently, diminishes the rate of respiration in mitochondria by inhibiting the oxidation of NADH-linked substrates. Id. The hypoglycemia-inducing activity of diphenyleneiodonium has been linked to the compound's ability to impair gluconeogenesis secondarily, via inhibition of mitochondrial NADH oxidation. Holland et al, "Mechanism of action of the hypoglycemic agent diphenyleneiodonium," J BIOL. CHEM. 218: 6050-59 (1973).

In addition, the oral administration of diphenyliodonium salts, such as diphenyliodonium chloride (DIC), is a proven means for selectively inhibiting microbial deamination in ruminant animals and, thereby, protecting aminated components in the animals' diet from ruminal fermentation. Chalupa, "Manipulating rumen fermentation," J. ANIMAL SCI. 46: 585-99 (1977). Chalupa et al, U.S. Pat. No. 3,862,333, specifically discloses a method for inhibiting the deamination of amino acids by rumen microbes, comprising the oral administration to a ruminant of an effective, nontoxic quantity of a diphenyliodonium salt. Broderick and Balthrop, "Chemical inhibition of amino acid deamination by ruminal microbes in vitro," J. ANIMAL SCI. 49: 1101-11 (1979), similarly conclude that DIC effectively inhibits deamination at very low ruminal concentrations, and suggest DIC's utility as a feed additive.

Thus, the above-summarized literature on the physiological effects of bivalent iodine compounds makes no mention of hemodynamic activity. In particular, disclosures in the art concerning a sodium nitroprusside-like effect by any species of diphenylhalonium ion are unknown.

SUMMARY OF THE INVENTION

Accordingly, it is an object of the present invention to provide a pharmaceutical composition which can be used in animals and humans to elicit sodium nitroprusside-like effects, including stimulation of guanylate cyclase activity in vivo.

It is another object of the present invention to provide a method for inhibiting the aggregation of blood platelets in mammals.

It is still another object of the present invention to provide a hemodynamic agent which can be used to enhance the contractility of cardiac muscle, for example, in the treatment of congestive heart failure.

It is a further object of the present invention to provide a method for relaxing vascular tone in systemic blood vessels, using an active ingredient which is capable of providing a diphenylhalonium ion in vivo.

In accomplishing the foregoing objects, there has been provided, in accordance with the present invention, in preferred embodiments of the present invention, the sodium nitroprusside-like effect comprises stimulating guanylate cyclase activity. In accordance with another aspect of the present invention, a composition is provided which is capable of supplying a diphenylhalonium ion in vivo for use in inhibiting blood platelet aggregation.

There has also been provided, in accordance with yet another aspect of the present invention, a method for increasing myocardial contractility in an animal or a human, using diphenylhalonium ion as the active agent.

Further objects, features and advantages of the present invention will become apparent from the following detailed description. It should be understood, however, that the detailed description and specific examples, while indicating preferred embodiments of the invention, are given by way of illustration only, since various changes and modifications within the spirit of the scope of the invention will become apparent to those skilled in the art from this detailed description.

DETAILED DESCRIPTION OF PREFERRED EMBODIMENTS

Figure 1:
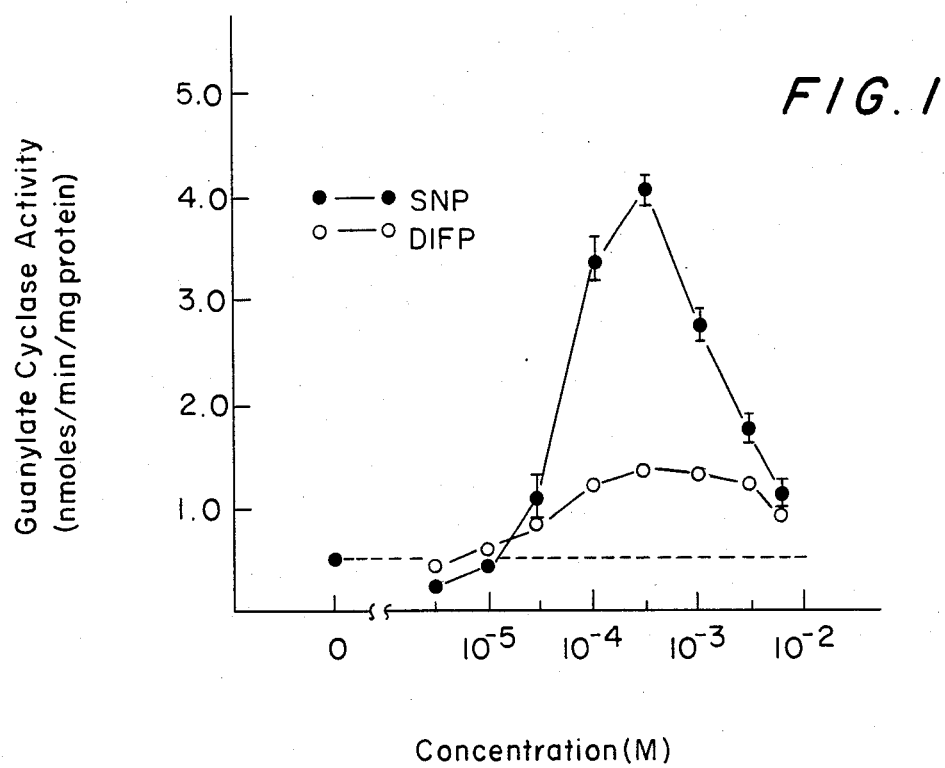
FIG. 1 shows the dose-related effect of diphenyliodonium hexafluorophosphate (DIFP) and SNP, respectively on soluble guanylate cyclase activity. Each point represents group mean±S.E. combined from two separate experiments (n=8).

Compounds capable of providing substituted or unsubstituted diphenylhalonium (DPHO) ion are known to the art. Methods for synthesizing dissociable diphenyliodonium, diphenylbromonium, and diphenylchloronium salts are disclosed, for example, by Nesmeyanov et al, "Diazybromonium salts from trifluorbromine and symmetrical azylcompounds of mercury," IZV. AKAD. NAUK SSSR, Ser. Khim. 255(5): 1136–40 (Russian) and Nesmeyanov et al, "Synthesis of diarylbromonium salts from $B_2F_3$ and azenes," IZV. AKAD. NAUK SSSR, Ser. Khim. 254(3): 652–56 (Russian), and in U.S. Pat. No. 3,151,175; No. 3,238,394; and No. 3,981,897. For the purpose of this description, "diphenylhalonium" is defined broadly enough to include a biphenyl-phenyliodonium structure, as disclosed by Koser et al, "New methodology in iodonium salt synthesis," J. ORG. CHEM. 45: 1543–44 (1980), and an oligomeric structure represented by the formula

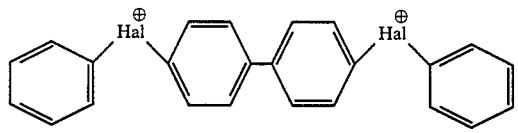

where Hal denotes halogen, as disclosed by Wiley and Salter, "Synthesis and carcinolytic activity of some diaryliodonium salts," J. MED. CHEM. 9: 228-31 (1966). The respective contents of each the documents cited in this paragraph are hereby incorporated by reference.

In general, the DPHO ion can be complexed, in accordance with the present invention, with an anion derived from a nontoxic, pharmaceutically acceptable inorganic or organic acid. The anion could be, for example, chloride, bromide, phosphate, hexafluorophosphate, iodide, dichloroiodate, hydroxide, sulfate, bisulfate, edisylate, nitrate, benzenesulfonate, methanesulfonate, tosylate, acetate, haloacetate, halosulfonate, propionate, benzoate, fumarate, maleate, lactate, citrate, picrate and tartrate. Because of their relative toxicity, fluoroborate, hexafluoroarsenate, and benzesulfonate salts are not recommended for use in humans.

Oral application of a DPHO-based compound is preferred in the present invention, although the combination of hydrophilic (halonium) and lipophilic (phenyl) moieties in the compound's structure renders it well-suited for topical application, for example, in combination with a lanolin-petrolatum base as a carrier. DPHO-based compounds can also be given intravenously, intramuscularly or subcutaneously since they are generally soluble, in therapeutically effective concentrations, in standard physiological solutions. Since DPHO-based compounds are generally light-sensitive, their preparations for parenteral administration should take into account a probable, gradual loss of efficacy in solution upon exposure to light. For example, a particular compound could be packaged as an anhydrous powder in a light-resistant glass vial and dissolved just prior to use in sterile buffered saline.

For topical applications, a DPHO-based compound could be combined in a lanolin-petrolatum base as an ointment and packaged, for example, in a tube or in an application patch containing a premeasured dose. Such an ointment, once applied, would be covered by an occlusive cellophane or paper dressing to enhance adsorption. Applied directly or in an application patch, the ointment would be applied to body skin covered by clothing to decrease the chance of photodecomposition.

For oral application, a DPHO-based compound can be combined in light-resistant gelatin capsules with an inert bulk filling agent, such as talc or kaolin. Similarly, for sublingual application, a DPHO-based compound can be combined in tablet form with a suitable filler and a binder which permits rapid dissolution of the tablet when the tablet is placed on the buccal mucose. In addition, a nonvolatile fixing agent, polyethylene glycol 4000, can be added to stabilize the DPHO-based tablet formulation. Preferably, carbohydrate-based fillers like lactose and starch 1500 should be avoided, since the halonium moiety may react with carbohydrates.

DHPO ion can stimulate guanylate cyclase activity, and thereby elevate cyclic GMP levels, in approximately the same concentration range (about $10^{-5}$ to $10^{-3}$M) as does SNP. The effect of DPHO ion on cyclic GMP levels is reflected in its ability to relax systemic vessels, thereby reducing arterial blood pressure and total peripheral resistance. Like SNP, DPHO ion can also inhibit blood platelet aggregation, possibly because of its SNP-like effect on guanylate cyclase activity. In addition, aside from its properties which parallel those of SNP, DPHO ion acts as an inotropic agent, increasing the contractility of cardiac muscle and, hence, the force of myocardial contractions.

The following examples illustrate, according to the present invention, DPHO's different pharmacological properties in standard laboratory preparations. The DPHO-based compound used in a iodonium salt, diphenyliodonium hexafluorophosphate (DIFP). Since the products of metabolism of DIFP in vivo may include a benzyl moiety, the use of unsubstituted DIFP in treating humans, in accordance with the present invention, is not recommended. Like other unsubstituted, DPHO-based compounds, DIFP is readily substituted at the bis-4 positions. Substitution at one or both of the 4-positions would make less likely the possibility that a benzyl moiety would be among the metabolic products of a DPHO-based compound. For example, modification to the bis-4-methyl form (metabolic product comprising a toluene moiety) should be considered for human applications. By the same token, either or both 4-positions of the DHPO ion can be substituted by ethyl, butyl, t-butyl, methoxy, ethoxy, amino, —CH$_3$SO$_2$, carboxyl, methylcarboxyl and/or ethylcarboxyl.

EXAMPLES 1

Stimulation of guanylate cyclase by DIFP

A. Measurement of guanylate cyclase activity

The conversion of [$^3$H]-guanosine triphosphate ([$^3$H]-GTP) to [$^3$H]-cGMP was assayed using a crude soluble preparation from rat lung, as adapted from the methods of Garbers and Murad, "Guanylate cyclase methods," ADV. CYCLIC NULEOTIDE RES. 10: 57-67 (1979), and Bohme et al, supra. Rats were anesthetized with sodium pentobarbital (Nembutal $^R$) and the lungs were perfused in situ with ice-cold 0.9% saline and quickly removed. The whitish lungs were then homogenized (Polytron-setting #6, 60 seconds) in ice-cold 25 mM TRIS/HCl (pH 7.6) containing 0.25M sucrose (5 ml/g tissue) and centrifuged at 105,000×g (4° C.) for 60 minutes. The cyclase reaction consisted of 25 mM TRIS-HCl (pH 7.6) containing isobutylmethylxanthine (3 mM), creatine kinase (33 units/ml), creatine phosphate (20 mM), MnCl$_2$ (3 mM), dithioreitol (5 mM), cGMP (1 mM), [$^3$H]-GTP (0.75 mM, 2.5×10$^6$ cpm/ml) and enzyme preparation (approximately 750 μg protein, as determined by the method of Lowry et al, "Protein measurement with the Folin phenol reagent," J. BIOL. CHEM. 193: 265-75 (1951)). The reaction was initiated by the addition of the [$^3$H]-GTP/MnCl$_2$/cGMP to tubes containing the remaining constituents, incubated for 15 minutes (37° C.) and terminated by adding 150 μml 0.4M zinc acetate followed by 150 μl 0.2M sodium carbonate. The tubes were frozen in dry ice/acetone, thawed and centrifuged (2500×g, 15 minutes) to precipitate unreacted [$^3$H]-GTP. The $^3$H-cGMP in the supernatant was isolated by ion-exchange column chromatography using polyethylenimine cellulose (Sigma Chemical Co., St. Louis, MO), as taught by Garbers and Murad, supra, and counted by liquid scintillation spectrometry at an efficiency of about 38%.

B. Stimulation of guanylate cyclase

As shown in Table 1 and in FIG. 1, respectively, both DIFP and SNP in the above-described assay activated rat lung guanylate cyclase in an concentration-dependent manner and in the same concentration range (approximately 10$^{-5}$ to 10$^{-3}$M), DIFP having about one-third the maximal activity of SNP. Both compounds produced peak effects at 300 μm, with a loss of activity at higher concentrations.

The guanylate cyclase-stimulating activity of DIFP was tested under several incubation conditions known to influence the activity of SNP. When the cyclase reaction was conducted without dithiothreitol, the activity of SNP was completely abolished, and the effects of DIFP were strongly inhibited. Similar results were obtained when the oxidant methylene blue was included, with the activity of both compounds being clearly reduced.

TABLE 1

Comparison of sodium nitroprusside (SNP) and diphenyliodonium hexafluorophosphate (DIFP) to activate guanylate cyclase: effects of dithiothreitol (DTT) or methylene blue.

| Treatment (μM) | Guanylate Cyclase Activity* | | | |
|---|---|---|---|---|
| | Control+ | (% Change) | (−DTT) | (% Change) |
| I. None | 0.36 ± 0.02 | (—) | 0.28 ± 0.03 | (—) |
| SNP (100) | 1.85 ± 0.22 | (+410) | 0.34 ± 0.03 | (+21) |
| SNP (300) | 2.59 ± 0.19 | (+720) | 0.25 ± 0.01 | (−11) |
| DIFP (3) | 0.23 ± 0.02 | (−36) | 0.22 ± 0.02 | (−21) |
| DIFP (10) | 0.35 ± 0.01 | (−3) | 0.30 ± 0.02 | (+7) |
| DIFP (30) | 0.71 ± 0.05 | (+97) | 0.41 ± 0.03 | (+46) |
| DIFP (100) | 1.31 ± 0.05 | (+260) | 0.50 ± 0.03 | (+79) |
| DIFP (300) | 1.51 ± 0.02 | (+320) | 0.56 ± 0.01 | (+100) |
| | Control+ | (% Change) | Methylene Blue (1 mM) | (% Change) |
| II. None | 0.42 ± 0.02 | (—) | 0.47 ± 0.03 | (—) |
| SNP (10) | 0.51 ± 0.02 | (+21) | 0.46 ± 0.06 | (−2) |
| SNP (30) | 0.62 ± 0.04 | (+48) | 0.46 ± 0.02 | (−2) |
| SNP (100) | 1.91 ± 0.07 | (+360) | 1.74 ± 0.04 | (+270) |
| SNP (300) | 4.27 ± 0.21 | (+920) | 1.18 ± 0.02 | (+150) |
| DIFP (3) | 0.46 ± 0.01 | (+10) | 0.51 ± 0.01 | (+9) |
| DIFP (10) | 0.63 ± 0.03 | (+50) | 0.53 ± 0.01 | (+13) |
| DIFP (30) | 0.97 ± 0.01 | (+130) | 0.71 ± 0.01 | (+51) |
| DIFP (100) | 1.46 ± 0.01 | (+250) | 0.91 ± 0.02 | (+94) |
| DIFP (300) | 1.50 ± 0.01 | (+260) | 1.02 ± 0.04 | (+120) |

*Values represent group means ± S.E. (n = 3) in pmoles/mg protein/min.
+Control groups contained 5 mM DTT during the 15 minute incubation.

EXAMPLE 2

Cardiovascular Effects of DPHO Ion

A. Measurement of cardiovascular function in dogs

Mongrel dogs, each weighing between about 10 and 20 kg, were anesthetized with Delvinal sodium (50 mg/kg), intubated, and ventilated with a Harvard volume-cycled ventilator. Catheters were placed from the femoral arteries retrograde into the left ventricle and mid-abdominal aorta to measure left ventricular and systemic arterial pressures, respectively. A Swan-Ganz thermister-tipped pulmonary artery catheter (American Edwards Laboratories, Santa Anna, CA) was placed from the right femoral or right external jugular vein into the pulmonary artery. DIFP was administered as a bolus intraveneous (i.v.) injection, while SNP was given by continuous infusion to obtain a sustained reduction in MAP.

Cardiac output (CO) was measured with an American Edwards 9520 A cardiac output computer using thermal dilution technique. Ten mls of ice-cold (1°–5° C.) 5% dextrose in water was injected as a bolus in the right ventricle on two occasions within 2 minutes, and the values averaged for the calculation of the CO. The abdominal aortic catheter was connected to a Hewlett Packard transducer, and blood pressure was recorded on a Hewlett Packard 77588 polygraph. Maximum left ventricular (1 V dP/dt) and left ventricular end diastolic pressure (LVEDP), were measured via the catheter inserted into the left ventricle through the right femoral artery. Cardiac contractility was measured as max dP/dt, or as max dP/dt divided by LVP at max dP/dt. Lead aVF electrocardiogram was monitored continuously and 5000 units of heparin were administered to avoid clotting. In addition to the directly obtained parameters, total peripheral vascular resistance (TPR dynes sec cm$^{-5}$) was calculated (as mean aortic pressure/CO$\times$80).

B. Reduction in MAP and enhancement of cardiac contractility

Figure 3:
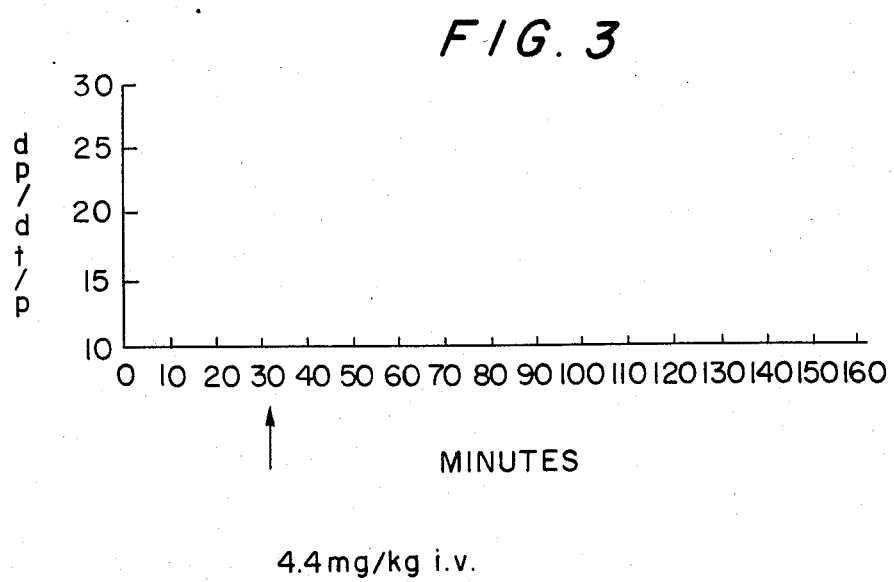
FIG. 3 shows the effect of DIFP on myocardial contractility in the anesthetized dog.
Figure 2A:
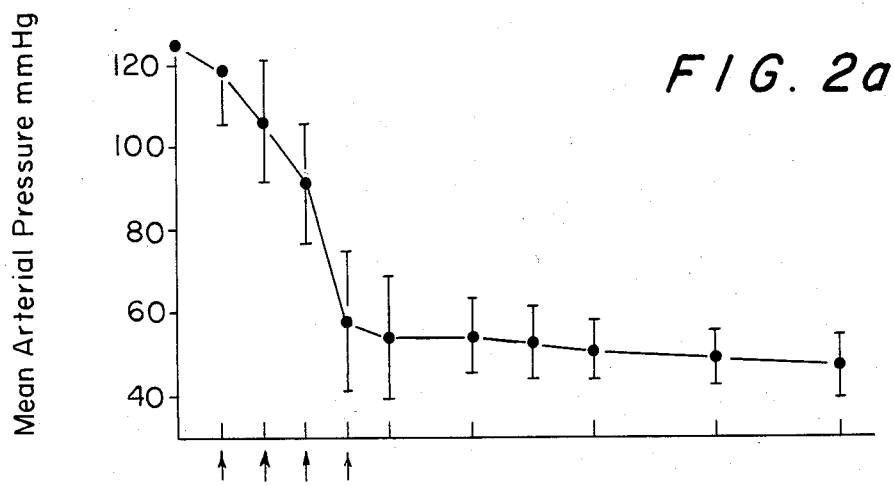
FIG. 2 depicts the cumulative dose-response of DIFP for three cardiovascular parameters in the anesthetized dog. Increasing amounts of DIFP were injected (i.v.) at the times indicated by the arrows to produce cumulative doses of 0.1, 0.4, 1.4, 4.4 mg/kg. Each point represents mean±S.E. (n=3).
Figure 2B:
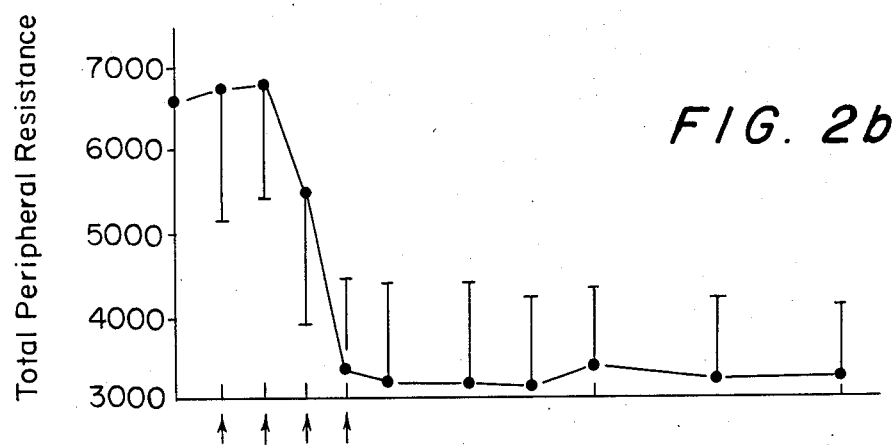
Figure 2C:
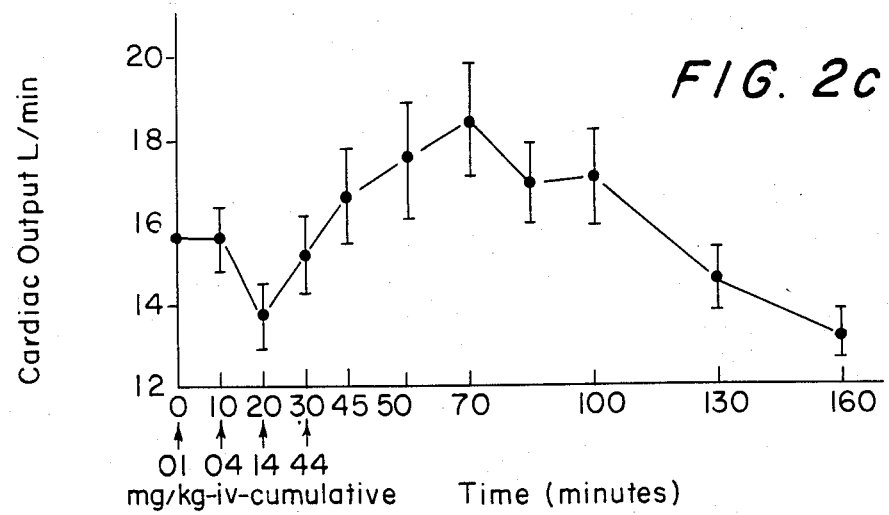

Mean systemic arterial pressure was reduced within 10 minutes after i.v. injection of DIFP. A cumulative dose of 4.4 mg/kg i.v., given over a 30-minute period, reduced MAP about 70 mmHg (FIG. 2A). There was no recovery in mean arterial pressure during the next 130 minutes. The fall in MAP was associated with a clear reduction in total peripheral resistance (FIG. 2B). Cardiac output (measured by thermal dilution) was transiently reduced during the injection period (FIG. 2C), but subsequently rose by the end of the injection period and reached maximum value at 70 min. The rate of ventricular contraction (dP/dt), normalized for left ventricular pressure, increased steadily after administration of DIFP (FIG. 3), indicating an increase in myocardial contractility.

Figure 4A:
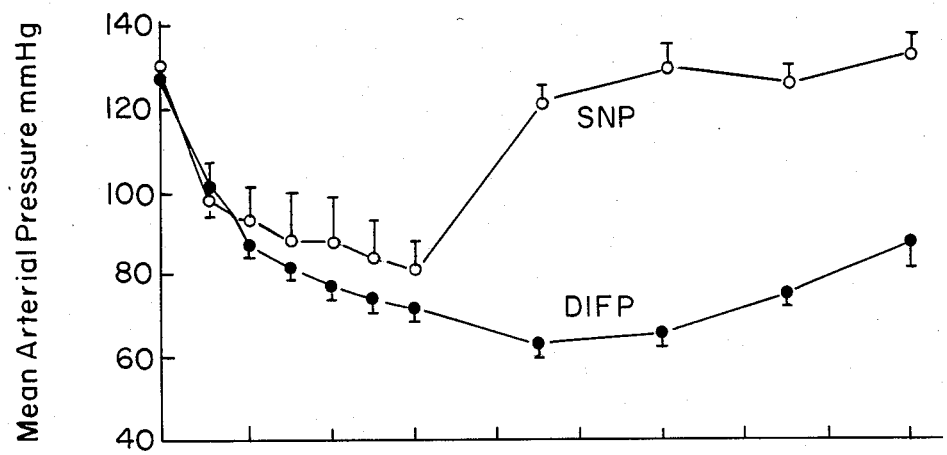
FIG. 4 shows the comparison of the cardiovascular effects of DIFP and SNP in the dog. SNP was administered as a 60-minute infusion (10 μg/kg/min) and DIFP was given as a bolus (1 mg/kg i.v.) at time zero. Values are group means±S.E. (n=3).
Figure 4B:
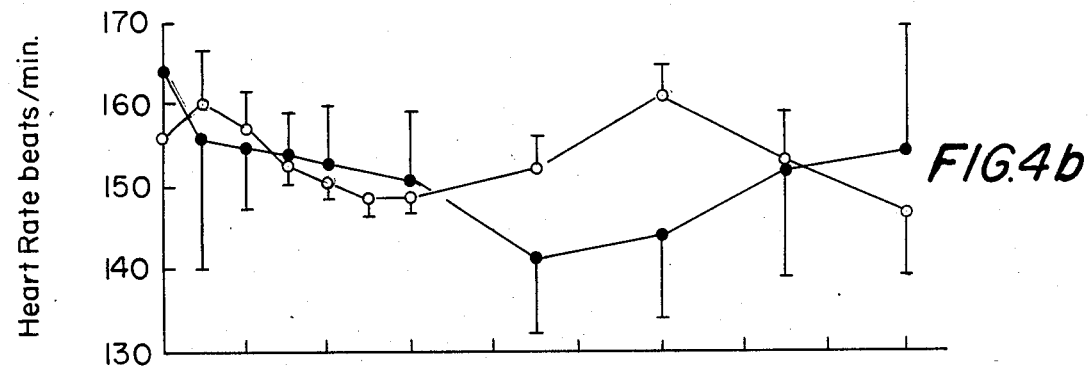
Figure 4C:
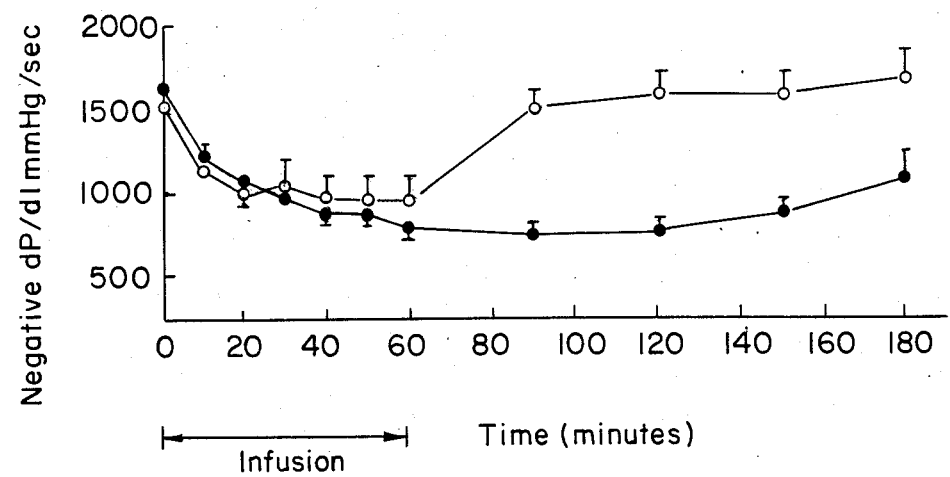

A 60-minute infusion with SNP (10 μg/kg/min) produced a maximal fall in MAP of comparable magnitude to 1 mg/kg (i.v.) DIFP given as a bolus (FIG. 4A). The effect of SNP persisted for as long as the infusion was maintained, but once the infusion was terminated, MAP returned to preinjection values within 20 minutes (FIG. 4A). The profile of the blood pressure response to SNP differed from that of DIFP, the latter producing a more gradual and longer lasting decline (3 hours) in MAP. In general, heart rate was lowered by about 10% for the duration of the 3-hour experiment (FIG. 4B). Negative dP/dt was also reduced by both SNP and DIFP, following an almost identical time course as that for MAP (compare FIGS. 4A and 4C).

What is claimed is:

1. A method for elevating GMP content in vivo, comprising the step of administering a composition comprising a therapeutically effective amount of an active ingredient selected from the group consisting of

wherein

Ar and AR' are phenyl which may be unsubstituted or substituted by one or more of the substituents selected from the group consisting of methyl, ethyl, butyl and t-butyl, the administered dosage of said active ingredient being sufficient to effect elevated intracellular cGMP levels in vivo.

2. The method of claim 1 wherein the active ingredient has the formula:

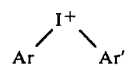

3. The method of claim 1 wherein the active ingredient has the formula:

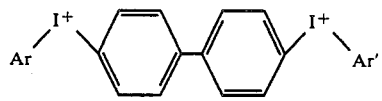

4. A method according to claim 1, wherein said active ingredient comprises said diphenylhalonium ion complexed with an anion derived from a nontoxic, pharmaceutically acceptable inorganic or organic acid.

5. A method according to claim 1, wherein said composition is administered orally.

6. A method according to claim 5, wherein ssaid composition is administered sublingually.

7. A method according to claim 1, wherein said composition is administered topically.

8. A method according to claim 1, wherein said composition is administered parenterally.

9. A method according to claim 8, wherein said composition is administered intravenously.

10. A method according to claim 8, wherein said composition is administered intramuscularly.

11. A method according to claim 8, wherein said composition is administered subcutaneously.

12. A method according to claim 1, wherein said composition comprises said active ingredient and a physiologically compatible drug carrier.

13. A method according to claim 1, wherein said cGMP levels are elevated to a degree that blood platelet aggregation in vivo is inhibited.

14. A method according to claim 1, wherein said cGMP levels are elevated in the vascular smooth muscle cells in vivo.

15. A method according to claim 1, wherein said cGMP levels are elevated in the platelet cells in vivo.

16. A method for treating a mammalian cardiovascular system, comprising the step of administering to an animal or human in need thereof a therapeutically effective amount of a composition comprising as an active ingredient a compound selected from the group consisting of

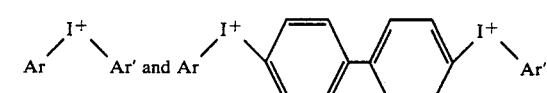

wherein

Ar and Ar' are phenyl which may be unsubstituted or substituted by one or more of the substituents selected from the group consisting of methyl, ethyl, butyl and t-butyl, the administered dosage of said active ingredient being sufficient to elicit enhanced myocardial contractility in said animal or human.

17. The method of claim 16 wherein the active ingredient has the formula:

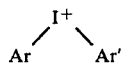

18. The method of claim 16 wherein the active ingredient has the formula:

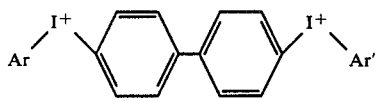

19. A method according to claim 16, wherein said active ingredient comprises said diphenylhalonium ion complexed with an anion derived from a nontoxic, pharmaceutically acceptable inorganic or organic acid.

20. A method according to claim 16, wherein said composition is administered orally.

21. A method according to claim 20, wherein said composition is administered sublingually.

22. A method according to claim 16, wherein said composition is administered topically.

23. A method according to claim 16, wherein said composition is administered parenterally.

24. A method according to claim 23, wherein said composition is administered intravenously.

25. A method according to claim 23, wherein said composition is administered intramuscularly.

26. A method according to claim 23, wherein said composition is administered subcutaneously.

27. A method according to claim 16, wherein said composition comprises said active ingredient and a physiologically compatible drug carrier.

* * * * *